United States Patent [19]

Nestor et al.

[11] 4,249,529
[45] Feb. 10, 1981

[54] SNAP-ACTION HOLDER FOR ENDOTRACHEAL TUBE WITH ONE-WAY QUICK TIGHTENING HEAD BANDS

[76] Inventors: Jack Nestor, 110 1st Ter., San Marine Is.; Lawrence M. Ciment, 3420 Chase Ave., both of Miami Beach, Fla. 33139; Abraham Rotbart, 5262 La Gorce Dr., Miami Beach, Fla. 33140

[21] Appl. No.: 85,746

[22] Filed: Oct. 17, 1979

[51] Int. Cl.³ .................. A61M 25/02; A61M 16/00
[52] U.S. Cl. .................. 128/207.17; 128/DIG. 26; 24/3 M; 24/241 P; 24/248 B; 24/252 B; 248/82; 248/84; 248/88; 248/62
[58] Field of Search .................. 128/200.26, 207.14, 128/207.15, 207.17, 346, 347, 348, 349 R, 349 BV, 349 B, 350 R, 350 V, DIG. 26; 248/538, 539, 540, 541, 82, 84, 88, 62, 63, 64, 92, 75; 211/68, 69.8; 24/3 R, 3 A, 3 J, 3 M, 137 A, 139, 241 P, 248 R, 248 B, 254 R, 257 R, 252 R, 252 B

[56] References Cited

U.S. PATENT DOCUMENTS

| | | | |
|---|---|---|---|
| 1,240,705 | 9/1917 | Grode | 211/68 |
| 2,908,269 | 10/1959 | Cheng | 128/207.14 X |
| 3,487,837 | 1/1970 | Peterson | 128/349 R |
| 3,774,616 | 11/1973 | White et al. | 128/200.26 |
| 3,924,636 | 12/1975 | Addison | 128/207.14 X |
| 3,993,081 | 11/1976 | Cussell | 128/207.14 |
| 4,071,930 | 2/1978 | Tanaka | 24/137 R |

Primary Examiner—Henry J. Recla
Attorney, Agent, or Firm—Erwin M. Barnett

[57] ABSTRACT

An endotracheal tube holder has a body which is secured by a pair of non-stretchable, head encircling straps to overlie the patient's mouth and portions of the cheeks. The straps, which are adapted to extend, one above and the other below, the patient's ears, have one-way tightening adjustability by pawl action. The body is integrally molded to incorporate a quick-acting clamp having three integral hinges, one hinge pivotally connecting a pair of jaws of the clamp and the other two hinges supporting the jaws from resilient arms for snap-action between open and closed positions. The clamp is operative to secure or release the endotracheal tube while the straps retain the body in position on the mouth against dislodgment.

10 Claims, 7 Drawing Figures

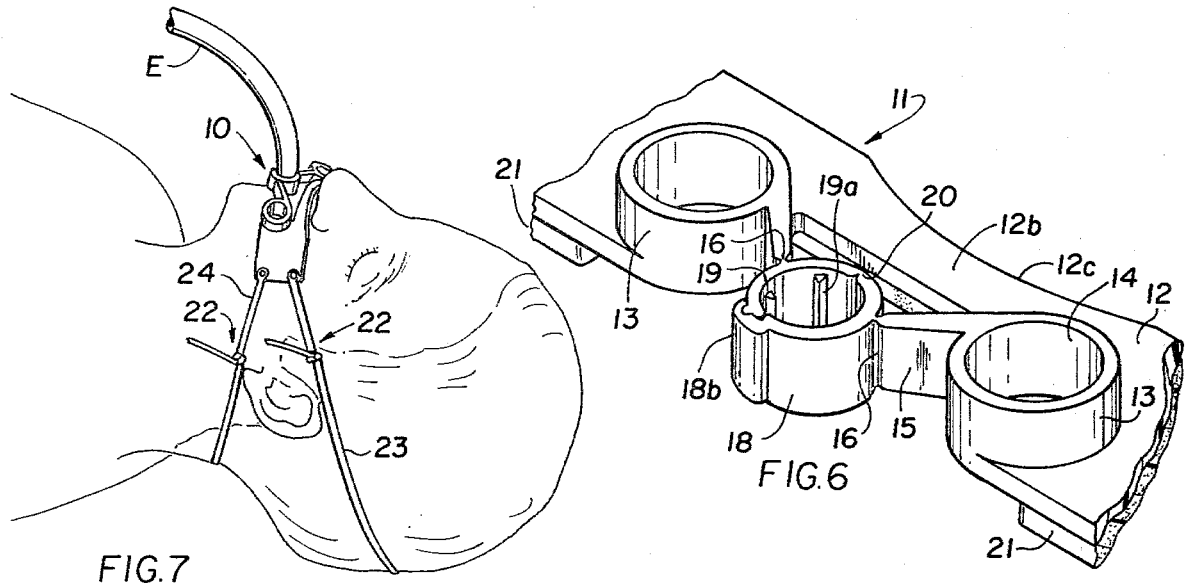
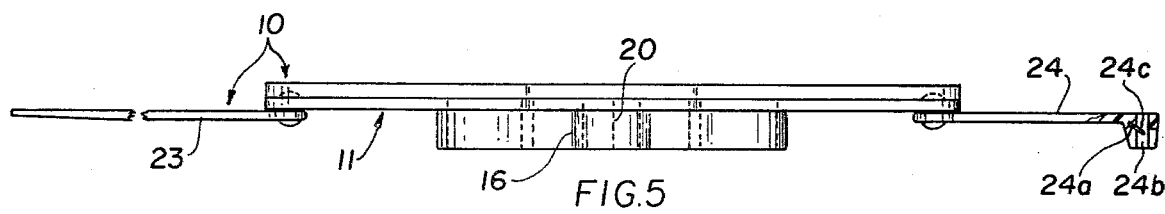
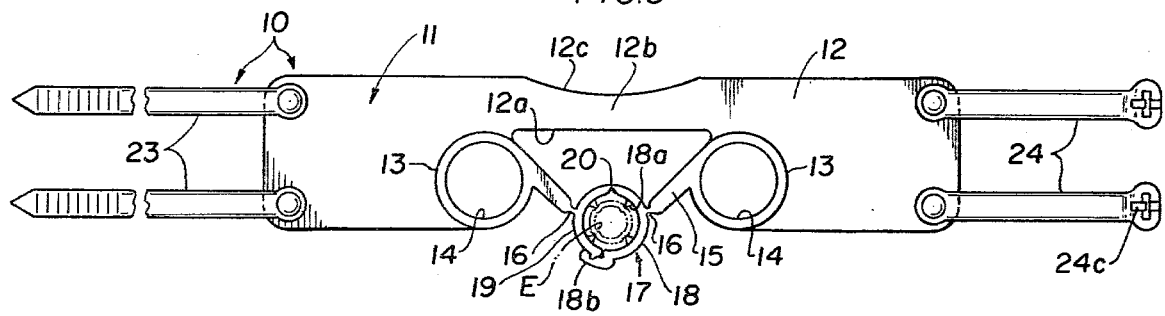
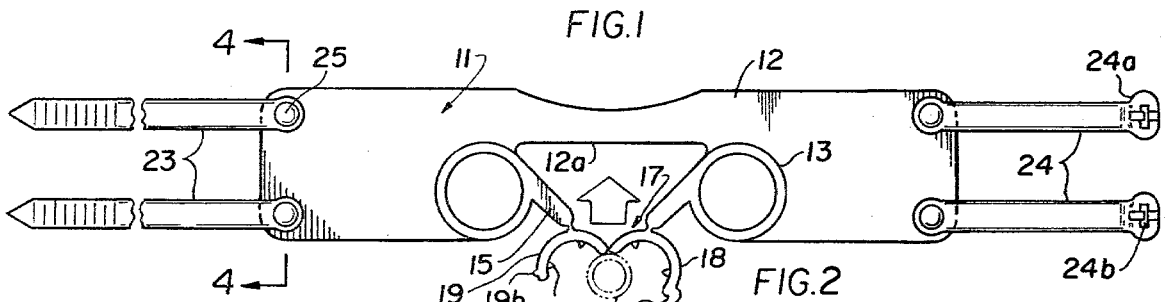
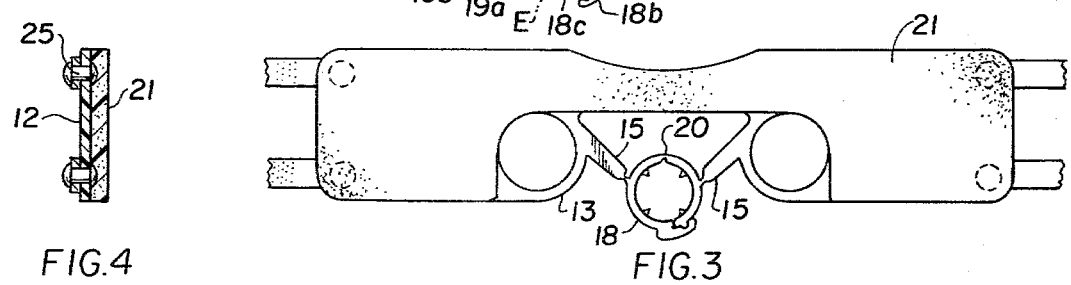

SNAP-ACTION HOLDER FOR ENDOTRACHEAL TUBE WITH ONE-WAY QUICK TIGHTENING HEAD BANDS

BACKGROUND OF THE INVENTION

1. Field of the invention

This invention relates to holders incorporating snap-action gripping means for releasably retaining endotracheal tubes in operative position, each holder being fitted to the patient's mouth and cheeks and having a pair of head encircling straps formed with one-way tightening means for retaining the holder in operative position against the patient's lips.

2. Description of the prior art

Various means have been devised for retaining an endotracheal tube in a desired mouth entering position against dislodgment by the patient's movements, both accidental or intentional because of discomfort. Surgical adhesive tape, as a most readily available expedient, has been widely used but has proved to be unsatisfactory by being difficult to apply properly, by coming off easily, by awkwardly catching the hair, by requiring removal and replacement by new adhesive tape when repositioning or adjusting the tube and by irritating the skin. Mechanical devices heretofore used have head encircling bands which either require hand tying or are made of an elastic material making positive positioning and retention of the holder on the patient's face a practical impossibility. In turn, the holders have inadequate means for gripping the tube, adding to the retention problem and failing to provide satisfactorily for adjustment of the tube on the patient.

There is, therefore, a present urgent need for an endotracheal or endoesophageal tube holder having a threefold capability, namely, that of quick and positive attachment to the patient's head which, after proper positioning on the lips and cheeks, will not readily be dislodged, that of easy releasable engagement of the tube for a firm grip by the holder to facilitate repositioning and adjustment of the tube on the patient without disturbing the mounting of the holder, per se, and that of providing comfort for the patient particularly where the holder is in facial contact with minimum irritation to the skin.

SUMMARY OF THE INVENTION

Among the objects of the invention is to provide an endotracheal tube holder which will eliminate the disadvantages of prior art devices and meet the needs hereinbefore described. The holder shall be relatively inexpensive to produce in quantity production as a one time use, disposable item and include the novel adaptation of an integral clip described in U.S. Pat. No. 3,292,223 modified as a snap-action releasable gripping means for positive engagement of the tube by the holder and the combination therewith of a pair of non-stretchable head encircling straps, each having a unidirectional catch for tightening-only adjustability as a quick and positive means for retaining the holder on the patient's mouth, the straps and catches being of a self clinching, pawl construction similar to those described, for example, in U.S. Pat. No. 3,186,047 or 3,537,146.

The endotracheal tube holder comprises a generally oblong-shaped body sized to extend across the patient's mouth between the nose and chin and to terminate at opposite sides thereof so as to overlie portions of the cheeks adjacent each side of the mouth. A pair of head encircling straps having one-way tightening adjustability are attached to opposite sides of the body, are fashioned of a non-stretchable material and are located so that one strap will extend above and the other below the patient's ears when encircling the head. Once tightened, the straps require severing for removal of the holder from the patient's head. The body may be molded of an elastomeric plastic material and formed with a central cutout located below a bridge portion adapted to overlie the patient's upper lip. The body incorporates a snap-action ring clamp located in the central cutout, which clamp grips the endotracheal tube passing therethrough into the patient's mouth. The clamp comprises a pair of arcuate shaped jaws integrally hinged together to form the ring when in closed position and adapted to swing apart at the hinge to an open position. Each jaw is supported at a midportion thereof for snap-action opening and closing by an integral hinge which terminates one of a pair of resilient arms which extend into the cutout in symmetrical spaced relation. The arm hinges are spaced apart a predetermined distance when the arms are in normal position retaining the jaws in either open or closed position. Application of a force is required to be applied to the jaws in a direction normal to a straight line between the arm end integral hinges to flex the arms and increase the predetermined distance to resiliently pivot the jaws on their interconnecting hinge enabling the performance of the snap-action between open and closed jaw positions.

BRIEF DESCRIPTION OF THE DRAWING

FIG. 1 is a front elevational view of the tube holder of the invention with the head encircling straps spread flat and the snap-action clamp shown in closed position, an endotracheal tube being indicated in a clamped position in broken lines.

FIG. 2 is a front elevational view of the tube holder shown in FIG. 1 with the snap-action clamp in open position, the endotracheal tube being indicated in broken lines in position for applying a force in the direction of the arrow to close the jaws of the clamp.

FIG. 3 is a rear elevational view of the tube holder shown in FIG. 1 showing the cushioning pad on the rear surface.

FIG. 4 is a sectional view taken on line 4—4 in FIG. 2 showing details of the attachment of the straps to the body.

FIG. 5 is a top view of the tube holder shown in FIG. 1.

FIG. 6 is an enlarged fragmentary perspective view of the tube holder in FIG. 1 showing the front and bottom sides of the central position of the body and details of the snap-action clamp, and FIG. 7 is a perspective view of a patient's head in a reclining supine position showing the tube holder of FIG. 1 and a portion of an endotracheal tube mounted in operative position.

DESCRIPTION OF THE PREFERRED EMBODIMENT

Referring in detail to the drawing, 10 generally denotes a tube holder embodying the invention for releasably retaining an endotracheal tube E or the like in operative position on the patient against accidental or voluntary dislodgment and is seen to comprise an oblong-shaped body 11, a cushioning rear pad 21 and a pair of head encircling straps 22, each formed as an adjustable length section 23 and a fixed length section 24.

Body 11 is molded as an integral unit, as for example, by injection molding methods, of a suitable elastomeric plastic resin, such as, linear polyethylene, polypropylene, or the like material, having tough foldable tear resistant properties satisfying the requirements for an integral hinge or pivot. Thus, integrally molded body 11 is seen in the drawings to comprise a flat rear or base plate 12 having a central cutout 12a formed below a bridge portion 12b having a concave upper edge 12c for better accommodating the patient's nose. A pair of cylindrical bosses 13 extend outwardly from base plate 12 and are symmetrically located below the opposite ends of bridge portion 12b bordering central cutout 12a. Bosses 13 are each formed with axial bores which align with similar openings in base plate 12 to provide passageways 14 through body 11 for the purpose hereinafter described. Each boss 13 has a tangential arm 15 which extends into central cutout 12a in a downward and medial direction toward each other in angular relation and terminates in a web 16 forming an integral hinge pivotally connecting thereto one of the arcuate shaped jaws 18 and 19 comprising snap-action ring clamp 17. Jaws 18 and 19, which are seen to connect to hinges 16 at midportions thereof, are in turn pivotally connected to each other by an integral hinge 20 located between hinges 16 for swinging between the closed position shown in FIGS. 1 and 6 and the open position shown in FIG. 2. Arms 15 resiliently retain clamp 17 in either open or closed position and are flexed apart when a force is applied to either open or close jaws 18 and 19 in the manner which is hereinafter described in more detail. To assist arms 15 in retaining jaws 18 and 19 in closed position, a finger nail manipulatable latch may be provided as a lip 18b projecting from jaw 18 to overlie the free end of jaw 19 when in closed position, lip 18b being formed with an interior groove 18c for snap-in engagement with rib 19b formed along the exterior surface of jaw 19. Jaws 18 and 19 may each be formed on the interior surface thereof with one or more spaced transverse ribs 18a and 19a, respectively, to improve the grip of clamp 17 on tube E and accommodate small difference in the OD of the latter.

In addition to the feature of the invention whereby tube E, extending into the patient's mouth, may be positively gripped by clamp 17 yet quickly released for adjustments or temporary removal thereof while body 11 remains in position, the invention also features quick tightening strap means whereby body 11 is in turn securely held in position on the patient's mouth against undesirable dislodgment. Accordingly, a pair of head encircling straps 22 are provided, one to extend above and the other to extend below the patient's ears for imparting stability to body 11. Each strap 22, made of a flexible and relatively non-stretchable plastic, such as, nylon, polypropylene or the like, has an adjustable length section 23 and a fixed length section 24 suitably attached at one end thereof to opposite side portions of body 11. Straps 22 resemble or may be adapted from so called bundling or cable straps or ties provided with integrally formed heads having openings through which the leading ends of the straps pass, the heads having pawl means for engaging the straps passing through the openings in a self clinching, strap tightening, one-way action in the manner described in the hereinbefore mentioned patents.

As seen in the drawing, the attachment to body 11 to adjustable length sections 23 and fixed length sections 24 is accomplished by rivets 25 located in the corners of body 11. Rivets 25 are shown in FIG. 4 as extending through suitable openings in end portions of strap sections 23 and 24 and base plate 12. It is understood that, as an alternative, suitable pins (not shown) may be integrally formed to project from base plate 12 and engage the openings in strap sections 23 and 24. Each fixed length section 24 terminates in an integral head 24a formed with a transverse opening or bore 24b sized and shaped to accommodate adjustable length section 23 passing therethrough. A tongue or pawl 24c is mounted in head 24a and extends in angular relation into opening 24b to engage adjustable length section 23. Tongue 24c is flexible for permitting movement of section 23 in a forward direction to tighten strap 22 and has a sharp transverse edge for engaging section 23 to prevent movement in a reverse direction to loosen strap 22. Tongue 24c is herein shown to be a metal insert molded into head 24a in the manner shown and described in the hereinbefore mentioned U.S. Pat. No. 3,186,047 or, as an alternative, adjustable length section 23 may be molded with integral teeth for for engagement with an intergral pawl formed in head 24a in the manner shown and described in U.S. Pat. No. 3,537,146 or other similar well known constructions.

Rear pad 21 may be made of a suitable cushioning material, such as, foam rubber, adhesively secured to the rear surface of base plate 12 and may have a cutout portion, as seen in FIG. 3, in the lower central area to expose the rear sides of clamp 17, bosses 13 including passageways 14, and arms 15.

The practical utility and operation of the tube holder 10 will now be apparent. As to the snap-action operation of clamp 17, it will be clear from FIGS. 1 and 2 that the normal rest positions of arms 15 locate hinges 16 at a predetermined distance from each other along a straight line or axis thereof requiring hinge 20 to be located at an extreme position above the axis of hinges 16 disposing jaws 18 and 19 in the fully closed position shown in FIG. 1, or requiring hinge 20 to be located at an extreme position below the axis disposing jaws 18 and 19 in the fully open position shown in FIG. 2. To urge jaws 18 and 19 from an open to a closed position, a force is applied normal to the axis of hinges 16, that is, along the line and in the direction of the arrow shown in FIG. 2, or in an opposite direction to the arrow to urge jaws 18 and 19 from a closed to an open position. In so doing, as hinge 20 approaches the axis of hinges 16, the greater effective length of jaws 18 and 19 causes hinges 16 to move further apart, that is, increases the predetermined distance, which movement is permitted by the flexing of arms 15 away from each other. As soon as hinge 20 passes through the axis of hinges 16, the resiliency of arms 15 snaps jaws 18 and 19 into the opposite extreme position, that is, to the closed position when hinge 20 is being moved upwardly or to the open position when hinge 20 is being moved downwardly.

It is intended that each tube holder 10, constructed as hereinbefore described and shown in the drawing, be packaged in an envelope in sterilized condition from which it is removed when ready for use. After the insertion and initial positioning of endotracheal tube E on the patient is completed, body 11 may be placed on the patient's mouth with clamp 17 in open position and tube E extending below open jaws 18 and 19 as indicated in FIG. 2. Adjustable length sections 23 of straps 22, which are provided in lengths sufficient to encircle the patient's head, are properly positioned, one passing above and the other below the ears, and the leading end of each section 23 is threaded through bore 24b in head 24a of the respective fixed length section 24, the latter being relatively short to conveniently locate head 24a forwardly of the patient's ear as seen in FIG. 7. The threading of section 23 through bore 24b, as will be clear from the sectional view of head 24a in FIG. 5, is performed from rear to front, tongue 24c permitting movement in this direction while locking section 23 against withdrawal movement in the opposite direction. Straps 22 may thus be shortened to an initial length encircling the patient's head while enabling any required readjustment of body 11 on the patient's mouth to be made prior to a final tightening of straps 22 against further dislodgment of body 11. This final tightening may be performed after tube E has been gripped by clamp 17 which is accomplished by pressing tube E upwardly against hinge 20 in the direction of the arrow as seen in FIG. 2. As hinge 20 passes through the axis of hinges 16, jaws 18 and 19 will snap into the closed position shown in FIGS. 1, 6 and 7, and rib 19b will also snap into engagement in groove 18c of lip 18b.

To release tube E from clamp 17, downward pressure is applied to tube E or directly to hinge 20 while simultaneously lifting lip 18b with a finger nail to facilitate disengagement between groove 18c and rib 19b. As hinge 20 passes through the axis of hinges 16, jaws 18 and 19 will snap into the open position shown in FIG. 2, releasing tube E for readjustment or removal. Where immediate use is no longer contemplated, holder 10 may be removed from the patient for disposal by severing straps 22 with a scissors or other suitable cutting instrument.

It is to be understood that lip 18b with its rib and groove engaging means is an additional locking expedient for preventing undesirable disengagement of tube E from body 11 by the patient and may be omitted without affecting the basic operation of holder 10 inasmuch as jaws 18 and 19 and arms 15 may be relied on to effectively grip and retain tube E in operative position.

Base plate 12 is sufficiently flexible and is aided by the cushioning effect of pad 21 to enable body 11 to conform to the contour of the patient's face. The relatively large rear surface area of pad 21 extending beyond the mouth and onto portions of the cheeks to more evenly distribute the pressure exerted by straps 22, the resilient softness of pad 21 and the properties of the foam rubber in resisting slippage all contribute to the comfort of the patient and to minimum skin irritation.

In keeping with the intended relatively permanent mounting by head encircling straps 22 of body 11, the positioning of bridge 12b on the patient's stationary upper lip permits movement of the lower jaw in opening and closing the mouth without disturbing the mounting of body 11. Likewise, in order to facilitate other functions requiring access to the patient's mouth, as for example, providing a suction tube for removing mouth secretions yet not interferring with the operation of clamp 17, passageways 14 are provided as axial bores through bosses 13.

Although two rivets 25 are provided on each end portion of base plate 12, one for each strap 22 located in the corners for better stability, it is to be understood that both straps 22 may be secured by a single rivet centrally located on each opposite end portion of base plate 12.

The endotracheal tube holder herein disclosed is seen to achieve the several objects of the invention and to be well adapted to meet conditions of practical use. As various possible embodiments might be made of this invention, and as various changes might be made in the disclosed holder, it is to be understood that all matters herein set forth or shown in in the accompanying drawing are to be interpreted as illustrative and not in a limiting sense.

What is claimed is:

1. A facial holder for an endotracheal tube having the capability of releasably retaining the tube in operative position extending into the patient's mouth, said holder comprising an oblong-shaped body sized to extend across the patient's mouth between the nose and chin and overlie portions of the cheeks adjacent each side of the mouth, a pair of head encircling straps connected to opposite sides of said body adapted for one strap to extend above and the other strap to extend below the patient's ears, said straps being non-stretchable and having one-way adjustable means for tightening the fit around the patient's head to secure said body in position on the patient's lips and cheeks and requiring severing of the straps for removal of the holder from the patient's head, said body being molded of an elastomeric plastic material formed with a central cutout located below a bridge portion adapted to overlie the patient's upper lip, a pair of resilient arms integral with said body and extending into said cutout in symmetrical spaced relation having ends spaced apart a predetermined distance when the arms are in normal position, a ring clamp for releasably gripping said tube as said retaining capability comprising a pair of arcuate jaws connected by an integral hinge for pivoting between open and closed tube clamping positions, an integral hinge connecting each of said arm ends to a midportion of one of said jaws the diameter of said ring clamp being at least equal to or greater than said predetermined distance whereby said ring clamp is supported for snap-action between said open and closed positions by application of a force to said jaws in a direction normal to a straight line between said arm end integral hinges, said force serving to flex said arms to increase said predetermined distance for passage of said first mentioned hinge therebetween in performing said snap-action.

2. The facial holder defined in claim 1 in which said jaws are integrally formed on the ends thereof opposite said first mentioned hinge with interengaging latch means adapted to snap into a locking position when the jaws are in closed position and being finger nail manipulatable for release of the jaws for said snap-action to the open position.

3. The facial holder defined in claim 2 in which said interengaging latch means comprises a lip formed to extend from one of said jaws to overlie the other jaw when in closed position, and snap-in rib and groove means formed on said other jaw and lip.

4. The facial holder defined in claim 1 in which said body includes a flat base plate having a flexibility to conform to the patient's face, said base plate having said central cutout, a pair of bosses extending outwardly from said base plate symmetrically located and bordering said central cutout, each of said arms being formed as an extension from one of said bosses.

5. The facial holder defined in claim 4 including a cushioning pad adhesively attached to the rear surface of said base plate.

6. The facial holder defined in claim 4 in which one of said bosses is formed with an axial bore aligning with a similar opening in said base plate providing an auxiliary passageway through said body for communicating the mouth with the exterior side of said body.

7. A facial holder for an endotracheal tube having the capability of releasably retaining the tube in operative position extending into the patient's mouth, said holder comprising an oblong-shaped body sized to extend across the patient's mouth between the nose and chin and overlie portions of the cheeks adjacent each side of the mouth, head encircling straps connected to opposite sides of said body adapted for retaining said body in said position on the patient's mouth, said body being molded of an elastomeric plastic material formed with a central cutout located below a bridge portion adapted to overlie the patient's upper lip, a pair of resilient arms connected with said body and extending into said cutout in symmetrical spaced relation having ends spaced apart a predetermined distance when the arms are in normal position, a ring clamp for releasably gripping said tube as said retaining capability comprising a pair of arcuate jaws connected by an integral hinge for pivoting between open and closed tube clamping positions, a hinge connecting each of said arm ends to a midportion of one of said jaws said jaws, hinges, arms and body being molded as an integral unit from said elastomeric plastic material, the diameter of said ring clamp being at least equal to or greater than said predetermined distance whereby said ring clamp is supported for snap-action between said open and closed positions by application of a force to said jaws in a direction normal to a straight line between said arm end integral hinges, said force serving to flex said arms to increase said predetermined distance for passage of said first mentioned hinge therebetween in performing said snap-action.

8. The facial holder defined in claim 7 in which said body includes a flat base plate having a flexibility to comform to the patient's face, said base plate having said central cutout formed therein, a pair of bosses extending outwardly from said base plate symmetrically located and bordering said central cutout, each of said arms being formed as an extension from one of said bosses, one of said bosses being formed with an axial bore aligning with a similar opening in said base plate providing an auxiliary passageway for introducing another tube therethrough into the patient's mouth, and a cushioning pad adhesively attached to the rear surface of said base plate.

9. The facial holder defined in claim 8 in which each of said bosses is cylindrical in shape and said arms extend in a tangential relation with respect to the boss thereof.

10. The facial holder defined in claim 7 in which the interior surface of each of said jaws is formed with a plurality of spaced transverse ribs for accommodating small differences in the endotracheal tube OD.

* * * * *